(12) United States Patent
Joos

(10) Patent No.: US 6,846,180 B1
(45) Date of Patent: Jan. 25, 2005

(54) THREADED INTRAOSSEOUS DENTAL IMPLANT

(75) Inventor: Ulrich Joos, Münster (DE)

(73) Assignee: Lipat Consulting AG, Basel (CH)

( * ) Notice: Subject to any disclaimer, the term of this patent is extended or adjusted under 35 U.S.C. 154(b) by 0 days.

(21) Appl. No.: 10/088,001

(22) PCT Filed: Sep. 22, 1999

(86) PCT No.: PCT/CH99/00452

§ 371 (c)(1),
(2), (4) Date: Mar. 14, 2002

(87) PCT Pub. No.: WO01/21091

PCT Pub. Date: Mar. 29, 2001

(51) Int. Cl.$^7$ ............................................. A61C 8/00
(52) U.S. Cl. ......................................................... 433/174
(58) Field of Search ................................ 433/174, 175, 433/172, 173, 220, 176

(56) References Cited

U.S. PATENT DOCUMENTS 5,603,616 A * 2/1997 Fernandes .................. 433/175
5,642,996 A * 7/1997 Mochida et al. ............ 433/174
5,984,681 A * 11/1999 Huang ........................ 433/174

FOREIGN PATENT DOCUMENTS

| DE | 40 41 378 | 6/1992 |
| DE | 195 45 014 | 6/1997 |
| NL | 8200711 | 9/1983 |

* cited by examiner

Primary Examiner—Melba Bumgarner
(74) Attorney, Agent, or Firm—Leydig, Voit & Mayer, Ltd.

(57) ABSTRACT

The screw-type intraossal dental implant has a bottommost implant tip that is located in the apical area and comprises a root part which extends up to said implant tip and which is intended for insertion into a jaw bone. The implant neck extending up to the coronal area is placed on the root part and is intended for being placed inside the gingivae. The outer thread on the root part is preferably self-cutting. The invention is characterized in that the root part comprises an essentially parabolic outer contour with the implant tip serving as the vertex. The inventive outer contour makes it possible to obtain an improved primary stability and guarantees, to a great extent, the long-term success of the implant.

13 Claims, 1 Drawing Sheet

Fig. 1
Fig. 2
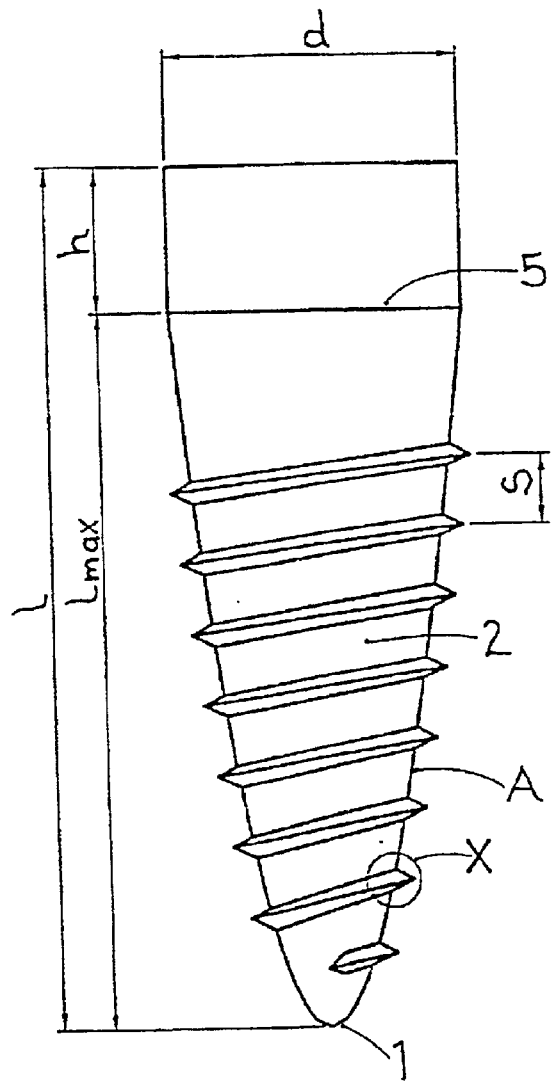
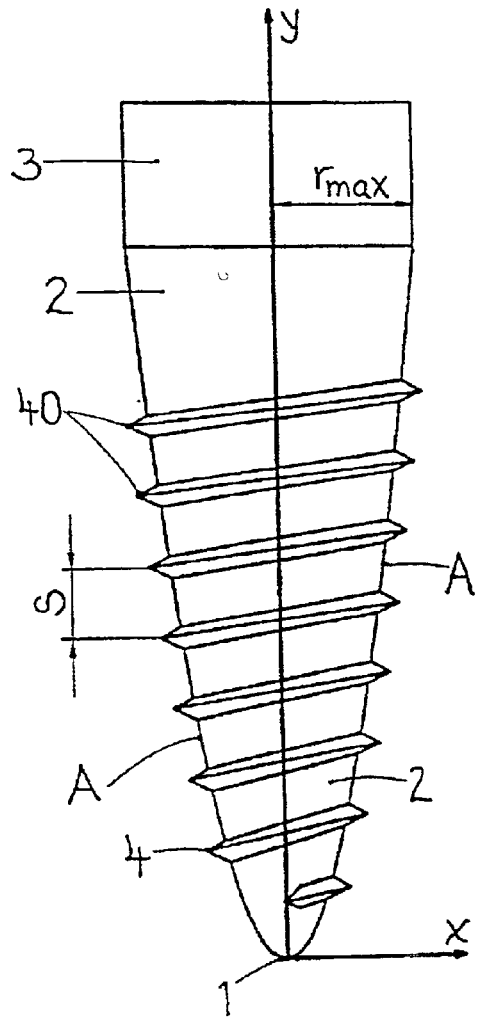
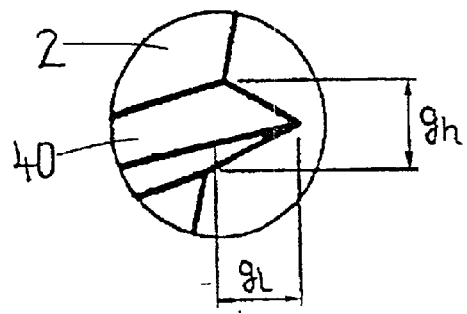
Fig. 3

THREADED INTRAOSSEOUS DENTAL IMPLANT

FIELD OF APPLICATION OF THE INVENTION

The present invention relates to a dental implant which is intended to be fitted in the jawbone and which has a thread on its outside. To this extent, the implant according to the invention differs generically from blade and cylinder implants as the other forms of intraosseous dental implants. In particular, the invention concerns the outer geometry of the implant, the measurement ratios of the implant body, and the characteristics of the outer thread, with the object of improving both primary and secondary stability and of thereby guaranteeing the long-term success of fitted implants.

PRIOR ART

Although this invention concerns dental implants, the shorter form "implant" will be used hereinafter for the sake of brevity. An overview of the implant forms commonly used in dentistry is given by H. Spiekermann in "Implantologie, Farbatlanten der Zahnmedizin" published by Georg Thieme Verlag Stuttgart and New York, 1994, vol. 10, page 15. Here, a differentiation is made between blade, cylinder and screw implants. The blade implants which may possibly be advantageous for very specific applications are not considered at all. The cylinder implants have a cylindrical body which is either continuous or stepped. The root part can have openings for better bone integration, and the implant tip lying at the apical end has the shape of a semisphere or a rounded summit. The root part has a rough or profiled surface produced by material application or removal. The implant neck or head is in most cases smooth.

The screw implants have an outer thread extending at least over most of the root part. Their implant bodies are likewise cylindrical with a semispherical, rounded, frustoconical or parabolic implant tip (see U.S. Pat. No. 4,626,214). Slightly conical forms are also known (see U.S. Pat. No. 4,713,003). The implant necks are in most cases also cylindrical at the transition from the root part, whereas in the coronal direction the heads taper conically, widen in a trumpet shape or have an external polygon.

The basically cylindrical shape of the root part has proven not best suited for obtaining the desired postoperative primary stability of the fitted implant. Moreover, the lifetime of the implants is in many cases inadequate: the fitted implant loosens early after just a few years. Investigations revealed that this early loosening is caused by bone resorption around the fitted implant, which is attributable to insufficient introduction of force to the bone via the existing implant forms. Bone expansions of between 1000 and 4000 microstrains are defined as relevant to remodeling. Values below 1000 microstrains are considered inadequate and result in reduced mineralization and formation of connective tissue. Values above 4000 microstrains are considered excessive and result in bone resorption (see Barbier, L. et al.: Finite element analysis of nonaxial versus axial loading of oral implants in the mandible of the dog, in J. Oral Rehabil. 1998, 25(11) :847–858).

OBJECT OF THE INVENTION

In view of these shortcomings of the dental implants known to date, it is an object of the invention to propose an implant form which contributes to increasing the primary stability of fitted implants so that the implant is immediately able to bear loads, both during the postoperative work involved in attaching the superstructures and also during use by the patient. Immediate ability to bear loads signifies the primary stability achieved immediately after implantation. However, it will be appreciated that in some cases it is advantageous to wait several days of the main wound-healing phase before actual loading of the implant. Moreover, an optimized implant form is intended to maintain the natural introduction of force into the bone, comparable to that in a real tooth, and thereby to guarantee the long-term success to a greater extent.

SUMMARY OF THE INVENTION

The dental implant has a bottommost implant tip located at the apex and a root part which extends to the implant tip and is intended to be fitted in the jawbone. Adjoining the root part there is the implant neck which extends in the coronal direction and, in the implanted state, comes to lie inside the gingiva. At least over some of the root part, the implant is provided with an outer thread, which can be self-cutting. The main feature is that the root part has a principally parabolic outer contour with the implant tip as vertex.

The description given below relates to preferred illustrative embodiments of the invention.

The root part and the implant neck adjoin each other on a theoretical ridge line, the root part having the maximum length $l_{max}$ extending in the axial y-direction. At the ridge line, the root part has the maximum radius $r_{max}$ extending in the radial x-direction. Placed in a Cartesian system of x-y coordinates, and with the implant tip positioned at the origin of this system, the parabolic outer contour follows the equation $$l_y = K \cdot 4r_x^2, \text{ with:}$$

$l_y$ as the respective ordinate value;
$r_x$ as the associated abscissa value; and
K as the constant resulting from the equation $$K = l_{max} : 4r_{max}^2.$$

The maximum radius $r_{max}$ is between 1.0 mm and 3.0 mm; it preferably lies in the range of from 1.5 mm to 2.0 mm. The maximum length $l_{max}$ of the root part correlates with the pitch of the outer thread, the latter ending at a distance from the ridge line. The distance is preferably 1.0 mm to 4.0 mm. This distance is defined by the thickness of the cortical zone on the marginal bone and by the length of the implant. In order to guarantee an optimum introduction of force into the bone in this area, the distance of the outer thread from the ridge line becomes greater as the length of the root increases. In addition, the distance contributes to excluding the very critical entry of bacteria into the implant bed.

At the root part, and extending in the y-direction, the thread teeth have a height in the region of 0.3 mm; and, extending in the x-direction, a length in the range of from 0.25 mm to 0.5 mm. The length of the m thread teeth decreases as the maximum length of the root part increases.

The implant is made of biocompatible material having suitable stability properties. Examples of these are titanium, titanium-based alloys, other metals or metal alloys, ceramic, glass ceramic or ceramic-like materials, and biocompatible plastics. The root part has a rough surface which is, for example, plasma-coated or ceramic-coated, or has been treated, for example, chemically, electrochemically, mechanically or by laser. An implant neck made of titanium or a titanium-based alloy is polished. The implant neck can also be coated with ceramic or with ceramic-like material or with hydroxyapatite. Measured in the y-direction, the implant neck has a height in the region of 2.0 mm and is cylindrical or widened or narrowed in a trumpet shape or conically in the coronal direction. The dental implant can be used either as a one-phase or two-phase implant.

BRIEF DESCRIPTION OF THE ATTACHED DRAWINGS

FIG. 1 shows a front view of an implant according to the invention;

FIG. 2 shows the implant according to FIG. 1 in a system of x-y coordinates; and FIG. 3 shows an enlargement of the detail X from FIG. 1.

EMBODIMENT

There follows a detailed description of an illustrative embodiment of the dental implant according to the invention, with reference to the attached drawings.

At the very bottom of the implant is the apically situated implant tip 1 to which the root part 2 extends from the coronal direction, which root part 2 is intended to be fitted in the jawbone. Adjoining the top of the root part 2, at the theoretical ridge line 5, is the implant neck 3 which extends in the coronal direction and is intended to lie inside the gingiva. From the implant tip 1 to a point below the ridge line 5, the root part 2 is provided with an outer thread 4 which is preferably self-cutting and has the pitch S. The outer thread 4 ends at a distance below the ridge line 5; the distance is preferably in the range of from 1.0 mm to 4.0 mm. The root part 2 has a substantially parabolic outer contour A with the implant tip 1 as vertex.

The following dimensions can be defined on the implant:

l→total length, for example 12.0 mm, extending in the axial y-direction, on the ordinate axis;

$l_{max}$→part of the total length l and maximum length of the root part 2;

h→apart of the total length l and height of the implant neck 3;

$r_{max}$→maximum radius of the root part 2 at the ridge line 5, extending in the radial x-direction, on the abscissa axis;

d→nominal diameter of the implant, which is derived from $2 \cdot r_{max}$;

$g_h$→height of the thread teeth 40 of the outer thread 4 on the root part 2, extending in the y-direction;

$g_l$→length of the thread teeth 40 in the x-direction.

If the implant is placed with its parabolic outer contour A in a Cartesian system of x-y coordinates and the implant tip 1 is positioned in this case at the origin of the system of coordinates, the outer contour A follows the equation $l_y = K \cdot 4r_x^2$. Here represent:

$l_y$→the respective ordinate value for forming the outer contour A;

$r_x$→the abscissa value associated with the ordinate value $l_y$, and

K→the constant which results from the equation $K = l_{max} : 4r_{max}^2$.

The maximum radius $r_{max}$ is between 1.0 mm and 3.0 mm, preferably lying in the range of from 1.5 mm to 2.0 mm. Thus, assuming for example that $r_{max}$=2.0 mm (nominal diameter of the implant d=4.0 mm), this gives the following values for the constant K and for the equations for determining the ordinate values $l_y$ and abscissa values $r_x$ of the outer contour A:

| Length $l_{max}$ of root part [mm] | $l_y$; $r_x$ | Constant K |
| --- | --- | --- |
| 6 | $l_y = K \cdot 4r_x^2$ | 0.375 |
| 8 | $l_y = K \cdot 4r_x^2$ | 0.500 |
| 10 | $l_y = K \cdot 4r_x^2$ | 0.625 |
| 12 | $l_y = K \cdot 4r_x^2$ | 0.750 |
| 14 | $l_y = K \cdot 4r_x^2$ | 0.875 |
| 16 | $l_y = K \cdot 4r_x^2$ | 1.000 |

The maximum length $l_{max}$ of the root part 2 correlates with the pitch S of the outer thread (4).

Thus, assuming for example that $r_{max}$=2.0 mm (nominal diameter of the implant d=4.0 mm) and assuming maximum lengths $l_{max}$, this gives the following relations for the pitch (S) of the outer thread 4:

| Length $l_{max}$ of root part [mm] | Pitch (S) [mm] |
| --- | --- |
| 6 | 0.65 |
| 8 | 1.00 |
| 10 | 1.00 |
| 14 | 1.00 |
| 16 | 1.00 |

The outer thread (4) at the root part (2) with its thread teeth (40) has the following values, for example:

extending in the y-direction, a height $g_h$ of the thread teeth 40 in the region of 0.3 mm; and extending in the x-direction, a length $g_l$ of the thread teeth 40 in the range of from 0.25 mm to 0.5 mm.

The length $g_l$ of the thread teeth 40 decreases as the maximum length $l_{max}$ of the root part 2 increases.

Thus, assuming for example $r_{max}$=2.0 mm (nominal diameter of the implant d=4.0 mm), this gives the following values for the outer thread 4 with its thread teeth 40:

| Length $l_{max}$ of root part [mm] | Height $g_h$ of thread teeth [mm] | Length $g_l$ of thread teeth [mm] |
| --- | --- | --- |
| 6 | 0.30 | 0.40 |
| 8 | 0.30 | 0.40 |
| 10 | 0.30 | 0.30 |
| 14 | 0.30 | 0.25 |
| 16 | 0.30 | 0.25 |

The implant is made of biocompatible material having suitable stability properties. Examples are titanium, titanium-based alloys, other metals, their alloys, ceramic, glass ceramic or ceramic-like materials, and biocompatible plastics. The root part 2 has a rough surface which, for example, is plasma-coated or ceramic-coated or is treated, for example, chemically, electrochemically, mechanically or by laser. An advantageous surface structure for the root part 2 is the subject of the invention in PCT publication WO 99/13700. The implant neck 3 can be made of titanium, a titanium-based alloy, another biocompatible metal or alloy and will then advantageously be polished. The implant neck 3 could be coated with ceramic, glass ceramic, ceramic-like material, hydroxyapatite, plastic or metal.

The implant neck 3 has, in the y-direction, a height h in the region of, for example, 2.0 mm. It is cylindrical or widens or narrows in a trumpet shape or conically in the coronal direction.

What is claimed is:

1. A dental implant comprising:
   a) a bottommost implant tip located at an apex;
   b) a root part which has a length, extends to the implant tip, is intended to be fitted in a jawbone, and has a parabolic outer contour which, when placed in a cartesian system of x-y coordinates, with the implant tip positioned at the origin, follows the equation $l_y = K \cdot 4r_x^2$, where
      $l_y$ represents a y coordinate value and $r_x$ represents an x coordinate value, and the constant K results from the equation $K = l_{max}/4r_{max}^2$;
   c) an implant neck adjoining the root part, which extends in a coronal direction and is intended to lie inside the gingiva; and
   d) an outer thread having a pitch and provided on the root part, wherein the root part has the parabolic outer contour along all of the length of the root part and as far as a theoretical ridge line at which the root part adjoins the implant neck, the root part at the ridge line having a maximum radius extending in a radial direction.

2. The dental implant as claimed in claim 1, wherein the outer thread provided on the root part has an outer contour extending parallel to the parabolic outer contour of the root part, and ends at a distance of 1 mm to 4 mm from the ridge line.

3. The dental implant as claimed in claim 1, wherein the maximum radius is between 1 mm and 3 mm.

4. The dental implant as claimed in claim 3, wherein the maximum radius is from about 1.5 mm to about 2 mm.

5. The dental implant as claimed in claim 1, wherein
   a) the outer thread is self-cutting;
   b) the length of the root part and the pitch of the outer thread correlate with one another as follows:

| Length of root part (mm) | Pitch (mm) |
| --- | --- |
| 6 | 0.65 |
| 8 | 1 |
| 10 | 1 |
| 14 | 1 |
| 16 | 1 | when the maximum radius of the root part at the ridge line is equal to 2 mm; and
   c) the outer threads ends at a distance in the y-direction of from 1 mm to 4 mm from the ridge line.

6. The dental implant as claimed in claim 1, wherein
   a) the outer thread includes thread teeth,
   b) the thread teeth at the root part extend in a y-direction, and have a height of about 0.3 mm; and
   c) the thread teeth, in an x-direction, have a length in the range from 0.25 mm to 0.5 mm.

7. The dental implant as claimed in claim 6, wherein
   a) the maximum radius is equal to 2 mm; and b) the thread teeth have the following values relative to the length of the root part:

| Length of root part (mm) | Height of thread teeth (mm) | Length of thread teeth (mm) |
| --- | --- | --- |
| 6 | 0.3 | 0.4 |
| 8 | 0.3 | 0.4 |
| 10 | 0.3 | 0.3 |
| 14 | 0.3 | 0.25 |
| 16 | 0.3 | 0.25. |

8. The dental implant as claimed in claim 1, wherein
   a) the implant is made of biocompatible material; and
   b) the root part has a rough surface which is treated by one selected from the group consisting of plasma-coating, ceramic-coating, chemical treatment, electrochemical treatment, mechanical treatment, and laser treatment.

9. The dental implant as claimed in claim 8, wherein the biocompatible material is selected from the group consisting of titanium-based alloys, metals, metal alloys other than titanium-based alloys, ceramic, and plastic.

10. The dental implant as claimed in claim 1, wherein the implant neck is polished and is made of a material selected from the group consisting of titanium, a titanium-based alloy, a biocompatible metal, and a biocompatible metal alloy other than titanium-based alloys.

11. The dental implant as claimed in 1, wherein
    a) measured in a y-direction, the implant neck has a height in the range from 1 mm to 3 mm; and
    b) the implant neck is cylindrical in the coronal direction.

12. The dental implant as claimed in claim 1, wherein the implant neck is polished and coated with a material selected from the group consisting of ceramic, glass ceramic, hydroxyapatite, plastic, and metal.

13. The dental implant as claimed in 1, wherein
    a) measured in a y-direction, the implant neck has a height in the range from 1 mm to 3 mm; and
    b) the implant neck has a dimension transverse to the coronal direction that changes in the coronal direction.

* * * * *